(12) United States Patent
Mitterer et al.

(10) Patent No.: US 8,148,502 B2
(45) Date of Patent: Apr. 3, 2012

(54) R-ALPHA1 ANTITRYPSIN ANION EXCHANGE CHROMATOGRAPHY

(75) Inventors: Artur Mitterer, Orth/Donau (AT); Meinhard Hasslacher, Vienna (AT); Christian Fiedler, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 376 days.

(21) Appl. No.: 11/693,609

(22) Filed: Mar. 29, 2007

(65) Prior Publication Data

US 2007/0260044 A1    Nov. 8, 2007

Related U.S. Application Data

(60) Provisional application No. 60/787,365, filed on Mar. 30, 2006.

(51) Int. Cl.
  *C07K 1/00* (2006.01)
  *C12Q 1/00* (2006.01)
  *C12P 21/04* (2006.01)

(52) U.S. Cl. .................. 530/412; 435/4; 435/70.1

(58) Field of Classification Search .............. None
See application file for complete search history.

(56) References Cited

U.S. PATENT DOCUMENTS 6,974,792 B2 * 12/2005 Mattes et al. ................. 435/219

OTHER PUBLICATIONS

George et al., Characterization of antithrombins produced by active site mutagenesis of human alpha 1-antitrypsin expressed in yeast, Blood, 1989, vol. 73, pp. 490-496.*
Ion Exchange Chromatography & Chromatofocusing; Principles and Methods, 2004.*
Brown et al., Studies on Mammalian Tyrosinase, The Journal of Biological Chemistry, 1958, vol. 233, pp. 77-80.*
Borregaard et al., Prevention of tissue damage: inhibition of Myeloperoxidase mediated inactivation of αl-proteinase inhibitor by N-acetyl cysteine, Glutathione, and Methionine, Agents and Actions, 1987, vol. 22, pp. 255-260.*
Bennett et al., Glucose-induced conformational change in yeast hexokinase, Proc. Natl. acad. Sci., 1978, vol. 75, pp. 4848-4852.*
Lomas et al., α1-antitrypsin Siiyama (Ser53→Phe), The Journal of Biological Chemistry, 1993, vol. 268, pp. 15333-15335.*
Pace et al., How to measure and predict the molar absorption coefficient of a protein, Protein Science, 1995, vol. 4, pp. 2411-2423.*
Thomas et al., Distribution coefficients of protein impurities in ferritin and lysozyme crystals Self-purification in microgravity, Journal of Crystal Growth, 2000, vol. 211, pp. 149-156.*
Rathore et al., Qualification of a Chromatographic Column, Mar. 2003, pp. 30-34, 36, 38, 40.*
Satoh et al., Emphysema associated with complete absence of alpha 1-antitrypsin of a stop codon in an alpha 1-antitrypsin-coding exon., Am. J. Hum. Genet., 1988, vol. 42, pp. 77-83.*
Morrison et al., The effect of reducing agents on proteolytic enzymes and oxidation of alpha 1-proteinase inhibitor., Biol. Chem Hoppe Seyler, 1986, Vo. 367, pp. 177-182.*
Uniprot P01009 (A1At_HUMAN). Last viewed on Oct. 28, 2010.*
Lomas et al., Effect of the Z Mutation on the Physical and Inhibitory Properties of alpha1-antitrypsin., Biochemistry, 1993, vol. 32, pp. 500-508.*
Curtis et al., Interaction of a trypsin-like enzyme of Porphyromomas gingivalis W83 with atithrombin III., FEMS Microbiology Letters, 1993, vol. 108, pp. 169-174.*
Mattes et al., Preparation and properties of an alpha-1-protease inhibitor concentrate with high specific activity., Vox. Sang. 2001, vol. 81, pp. 29-36.*
Chen et al., Purification of alpha 1 proteinase inhibitor from human plasma fraction IV-1 by ion exchange chromatography., Vox. Sang. 1998, vol. 74, pp. 232-241.*
Mahadeva et al., Alpha1-antitrypsin deficiency, cirrhosis and emphysema., Thorax, 1998, vol. 53, pp. 501-505.*
Definition of Hexokinase A (last viewed on Apr. 8, 2011).*
Murakami et al., Identification of the cDNA for Human Red Blood Cell-Specific Hexokinase Isozyme., Blood, 1997, vol. 89, pp. 762-766.*
Bergmeyer, et al., "Reagents for Enzymatic Analysis," Methods of Enzymatic Analysis vol. 11, Third Edition, 1963, pp. 222-223.
Karlsson, et al., "Ion-Exchange Chromatography," Protein Purification: Principles, High Resolution Methods, and Applications Edited by : Jan-Christer Janson and Lars Rydén, Second Edition, 1998, pp. 145-205.
Katti and Gulochon, "Fundamentals of Nonlinear Chromatography: Prediction of Experimental Profiles and Band Separation," Advances in Chromatography, 1992, vol. 31, pp. 1-118.
Shukla, A. "Bioseparations by Displacement Chromatography," Separation Science and Technology, 2000, vol. 2, pp. 379-415.
Veeraragavan, et al., "Sample displacement mode chromatogoraphy: purification of proteins by us of a high-performance anion-exchange column," Journal of Chromatography, 1991, vol. 541, pp. 207-220.

* cited by examiner

*Primary Examiner* — Alexander Kim
(74) *Attorney, Agent, or Firm* — Morgan, Lewis & Bockius, LLP (57) ABSTRACT

The present invention relates to a method for obtaining highly purified recombinant alpha1-antitrypsin (rAAT) using anion exchange chromatography, wherein a composition comprising rAAT and at least one impurity originating from cultivation of cells used for generating of rAAT is loaded onto a column containing anion exchange material and the anion exchange chromatography is carried out with buffers containing phosphate ions and N-acetylcysteine.

13 Claims, 5 Drawing Sheets

R-ALPHA1 ANTITRYPSIN ANION EXCHANGE CHROMATOGRAPHY

CROSS-REFERENCES TO RELATED APPLICATIONS

This application claims the benefit of U.S. Provisional Patent Application No. 60/787,365, filed Mar. 30, 2006, the disclosure of which is hereby incorporated by reference in its entirety for all purposes.

FIELD OF THE INVENTION

The present invention relates to a method for obtaining highly purified recombinant alpha 1 antitrypsin (rAAT) using anion exchange chromatography, wherein a composition comprising rAAT and at least one impurity originating from cultivation of cells used for generating of rAAT is loaded onto a column containing anion exchange material and the anion exchange chromatography is carried out with buffers containing phosphate ions and N-acetylcysteine (NAC).

BACKGROUND OF THE INVENTION

Displacement chromatography has been developed in the middle of the 20$^{th}$ century mainly for the separation of anorganic metal ions or rare earth elements, organic substances, and later also for small biomolecules like antibiotics, amino acids and peptides. At the beginning of the 80s this type of chromatography has begun to be applied for the separation of proteins. The theory and practical examples are summarized in various reviews, like Katti et al. 1992 (Katti A. M., Guichon G. A. Fundamentals in Nonlinear Chromatography: Prediction of experimental Profiles in "Advances in Chromatography" (J. C. Gidding, E. Grushka, P. R. Brown, eds.) Vol 31, pp. 1-118, 1992), Shukla et al. 2000 (Shukla A. A., Cramer S. M. Bioseparation by Displacement Chromatography in "Handbook of Bioseparations" (Ajuha S. ed.) Vol 2, pp. 379-415, Academic Press 2000) or Karlsson et al. 2000 (Karlsson E., Rydén L., Brewer J. Ion Exchange Chromatography in "Protein Purification" (Janson J-Ch., Rydén L. eds.) second edition, pp. 154-206, Wiley-Liss 1998).

In chromatography different modes of elution exists including isocratic elution, gradient elution and displacement. In displacement chromatography the column is eluted with a substance, the displacer (usually of low molecular weight) with a high affinity for the adsorbent (resin), whereas other substances (e.g. product and impurities) move at the same velocity through the column ahead of the displacer forming rectangular zones that follow each other in a train. An alternative mode of displacement chromatography is also called sample displacement chromatography (Veeraragavan K., Bernier A., Braendli E. 1991, Sample displacement mode chromatography: purification of proteins by use of a high-performance anion-exchange column, J. Chromatogr. Vol 541: 207-220)).

In all versions of chromatography, non-linear effects are common. These are seen as concentration-dependent retention times and asymmetric (e.g. tailing or fronting) peaks. Asymmetric peaks can result from a number of other causes as well, i.e. large extra-column volumes. In many applications, non-linear effects are disadvantageous as they decrease peak resolution and disturb quantitative evaluation. However, in preparative chromatography, heavy overloading is employed in order to increase material throughput, leading to prominent non-linear effects. A comprehensive text on non-linear chromatography has been published by G. Guiochon, S. Golshan Shirazi and A. M. Katti, Fundamentals of Preparative and Non-linear Chromatography, Academic Press, Inc. Boston (1994).

Alpha 1 antitrypsin (AAT) is intended to be used for patients suffering from genetically alpha 1 antitrypsin deficiency that can cause severe lung disease (known as hereditary emphysema). Currently, the only drug treatment available is a plasma derived AAT infused weekly requiring large doses to get therapeutic amounts of the protein to the lung where it is most needed. A recombinant AAT (rAAT) has been developed that is produced in bakers yeast Saccharomyces cerevisia without addition of any human or animal derived raw materials in the fermentation process, during the purification, and in the final formulation. The rAAT is intended to be delivered to the lung of the patients using a nebulizer. To avoid immunogenic reactions, in particular against residual amounts of the yeast host cell proteins, an rAAT product with high purity is required, especially in combination with high doses.

Thus, a strong need exists for a reliable method for obtaining highly purified rAAT. The present invention meets these and other needs.

SUMMARY OF THE INVENTION

Therefore, it is an object of the present invention to provide a new method for obtaining highly purified rAAT by means of anion exchange chromatography.

One embodiment of the invention provides methods for obtaining highly purified recombinant alpha 1-antitrypsin (rAAT) from a composition comprising the rAAT and at least one impurity originating from cultivation of cells used for generating rAAT. The methods comprise (i) loading a composition comprising rAAT and at least one impurity onto a column comprising an anion exchange material;

(ii) washing the anion exchange material using a buffer A comprising about 1 to about 80 mM phosphate ions and about 0.1 to about 50 mM N acetylcysteine (NAC);

(iii) eluting the rAAT from the anion exchange material using a gradient starting with an a buffer composition comprising 100% (v/v) of buffer A and ending with a buffer composition comprising 100% (v/v) buffer B within about 5 to about 100 column volumes (CV), wherein buffer B comprises about 50 to about 1000 mM phosphate ions and about 0.1 to about 50 mM NAC, thereby generating an eluent comprising fractions containing purified rAAT; and (iv) pooling the fractions containing the purified rAAT.

In some embodiments, the at least one impurity is an impurity originating from cells used for generating rAAT. In some embodiments, the at least one impurity is a yeast cell protein. In some embodiments, the at least one impurity is selected from: 12 kDa heat shock protein, YOL09wp, dihydrolipona-mide dehydrogenase, ribose 5-phosphate isomerase, rAAT fragments, cystathionine gamma-lyase, glucokinase, O-acetylhomoserine sulfhydrylase, rAAT-dimer, argininosuccinate lyase, 2-hydroxyacid dehydrogenase, hexokinase A. In some embodiments, the anion exchange material is selected from the group consisting of Q Sepharose HP, Cellufine Q, SourceQ, Fractogel EMD DEAE and Toyopearl QAE. In some embodiments, buffer A has a pH of about 6 to about 9 and buffer B has a pH of about 6 to about 9. In some embodiments, buffer A and buffer B have the same pH. In some embodiments, step (i) comprises loading about 2 to 50 mg/rAAT per ml anion exchange material onto the column. In some embodiments, step (iii) comprises eluting the rAAT from the anion exchange material using a gradient from a buffer composition comprising 100% (v/v) of buffer A to a buffer composition comprising 100% (v/v) buffer B within about 30 CV. In some embodiments, the starting point for the pooling in step (iv) is determined by UV absorption of the eluent at a wavelength in the range of 340 nm to 430 nm and the end point for the pooling is determined by UV absorption of the eluent at 280 nm. In some embodiments, The method according to claim 10, wherein the rAAT fraction pooling starts when the UV absorption at 395 nm of the sharp peak just preceding the rAAT main peak has declined to less than 10% of the maximum absorbance and wherein the rAAT fraction pooling is terminated when the UV absorption at 280 nm has declined to 40% of the UV absorption monitored at the beginning of the pooling.

In some embodiments, step (i) comprises loading about 10 to 30 mg/rAAT per ml resin onto a column having a diameter of about 80 to 120 cm and comprising a 34 µm mean Q Sepharose HP having a bed height of 24±2 cm and a packing of >5000 plates/meter;

step (ii) comprises washing the anion exchange material with a buffer A comprising 30 mM sodium phosphate and 3 mM N acetylcysteine (NAC) at a pH of 7.7; and step (iii) comprises eluting the rAAT from the anion exchange material using a linear gradient, starting with a buffer composition comprising 100% (v/v) of buffer A and ending with a buffer composition comprising 50% (v/v) of buffer A and 50% (v/v) of buffer B, wherein buffer B comprises 150 mM sodium phosphate and 3 mM NAC at a pH of 7.7; and step (iv) comprises pooling the fractions containing the purified rAAT, wherein the rAAT pooling starts when the UV absorption at 395 nm of the sharp peak just preceding the rAAT main peak has declined to less than 10% of the maximum absorbance, and the rAAT pooling is terminated when the UV absorption at 280 nm has declined to 40% of the UV absorption monitored at the beginning of the pooling.

DETAILED DESCRIPTION OF THE INVENTION

I. Introduction

The present invention relates to a method for obtaining highly purified recombinant alpha 1-antitrypsin (rAAT) by means of an anion exchange chromatography, e.g. using Q Sepharose HP as anion exchange material, wherein (i) a composition comprising rAAT and at least one impurity originating from cultivation of cells used for generating rAAT, is loaded onto a column containing an anion exchange material, (ii) the anion exchange material is washed using a buffer A containing phosphate ions and N-acetylcysteine and (iii) rAAT is eluted from the anion exchange material using a gradient of buffers A and B both containing phosphate ions and N-acetylcysteine (NAC). According to the method of the present invention, the impurities may be host cell impurities or more specifically may be yeast cell protein (YCP) impurities.

Herein, the expression "highly purified rAAT" means, for example, a purity of rAAT of higher than 99% w/w of total protein. The content of the at least one impurity is, for example, below 1%, preferably below 0.5%. The percentage values of the impurities refer to weight/weight of product, i.e. rAAT, and can be measured, for example, by HPLC or by the determination of the rAAT antigen or impurity protein antigen by ELISA. The present invention employing the elution with a phosphate gradient provides a method to reduce the content of the at least one impurity to about 50% or less compared to an elution with a gradient of one or more other salts than phosphate, preferably to about 40% or less, most preferably to about 30% or less, even more preferably to about 20% or less, and most preferably to about 10% or less. For example, the content of a combination of yeast cell proteins can be reduced to about 50% or less, preferably to about 40% or less, most preferably to about 30% or less, even more preferably to about 20% or less, and most preferably to about 10% or less, compared to the elution with a NaCl gradient in a Tris buffer. The content of the combination of yeast cell proteins can be determined, for example, by using the respective immunoglobuline combination in an ELISA (see, e.g., Example 2). Yeast hexokinase activity can be reduced by the method according to the invention to less than 50%, preferably to about 40% or less, most preferably to about 30% or less, even more preferably to about 20% or less, and most preferably to about 15% or less, compared to an elution with a NaCl gradient in a Tris buffer. The hexokinase activity can be determined, for example, by an enzymatic activity assay as described, for example, in Example 2. The comparative amounts of the impurities given above refer to amounts measured by the same method. For example, if the content of an impurity of a rAAT preparation purified by an elution using a gradient of one or more salts other than phosphate is determined by HPLC, the respective reduced amount of said impurity in a preparation purified by the method of the present invention is also measured by HPLC. However, this refers only to the comparison of one single parameter. Different parameters can be compared even if measured by different methods, as e.g. the amount of YCP (measured by ELISA) in relation to the amount of rAAT (measured by HPLC), see Table 2.

According to the present invention, the term "recombinant alpha 1-antitrypsin" (rAAT) does not underlie a specific restriction and may include any rAAT obtained via a recombinant DNA technology, or a biologically active derivative thereof.

As used herein, the term "biologically active derivative" includes any derivative of a protein, protein complex or polypeptide having substantially the same functional and/or biological properties of rAAT such as binding properties, and/or the same structural basis, such as peptidic backbone. Minor deletions, additions and/or substitutions of amino acids of the polypeptide sequence of rAAT which are not altering the biological activity of said polypeptide are also included in the present application as biologically active derivatives.

The rAAT according to the present invention may be derived from any vertebrate, e.g. a mammal. In one specific example of the present invention, the rAAT is human rAAT.

The rAAT according to the present invention may be produced by any method known in the art. This may include any method known in the art (i) for the production of recombinant DNA by genetic engineering, e.g. via reverse transcription of RNA and/or amplification of DNA, (ii) the introduction of recombinant DNA into prokaryotic or eukaryotic cells by transfection, e.g. via electroporation or microinjection, (iii) the cultivation of said transformed cells, e.g. in a continuous or batchwise manner, (iv) the expression of the rAAT, e.g. constitutive or upon induction, and (v) the isolation of the protein, e.g. from the culture medium or by harvesting the transformed cells, in order to obtain crude rAAT. Additionally, the recombinant DNA coding for rAAT, e.g. a plasmid, may also contain a DNA sequence encoding a selectable marker for selecting the cells which have been successfully transfected with the recombinant DNA. In one specific example of the present invention the cells used as host cells for producing rAAT are yeast cells.

According to one example of the present invention, crude rAAT is obtained from harvested cultured cells according to any method known in the art, e.g. by applying the steps of cell disruption by high pressure homogenization, clarification by micofiltration and a chromatographic capture step (e.g. on Q Sepharose XL).

According to another example of the present invention, crude rAAT may be further purified (pre-purified) using any purifying method known in the art, e.g. by metal chelate affinity chromatography such as copper chelating Sepharose Fast Flow (IMAC), optionally followed by one or more steps selected from the group consisting of the steps of negative chromatography on Phenyl Boronate Prosep (PB) resin, concentration by ultrafiltration and buffer exchange by diafiltration.

According to one example of the present invention, prepurification is carried out according to the following steps:

1. rAAT Capture—Anion Exchange Chromatography (Q-Sepharose XL Resin)

The function of this process step is to provide a crude purification and concentration of the diluted, clarified extract. After equilibration of the resin the diluted clarified extract containing the product is loaded onto the column that is fitted with two sets of guard filters operated in series. A wash step with a buffer containing about 70 mM NaCl removes part of the host cell impurities. Then, the product is eluted using a buffer containing approximately 160 mM NaCl.

2. Immobilized Metal Affinity Chromatography (Chelating Sepharose Fast Flow Resin)

The function of this process step is to provide a primary purification of the Capture column pool. The column is operated in a pseudo-affinity mode: chromatographic conditions are selected that allow for preferential binding of soluble AAT to the chelated $Cu^{2+}$ ions bound to the resin matrix. After charging and conditioning the column with copper ions and imidazole, the product contained in the capture pool is treated with NaCl and is subsequently loaded onto the column. Bound host cell impurities are removed from the column applying a series of two wash steps using buffers containing 300 mM NaCl and 300 mM NaCl plus 6.5 mM imidazole, respectively. The product is eluted from the resin with a buffer containing 20 mM imidazole.

3. Phenyl Boronate Flow-through Chromatography

The primary function of this process step is to separate glycosylated host cell protein contaminants. The column is operated in a "negative chromatographic" mode: host cell impurities are removed by chromatographic retention via selective interaction with the resin matrix, while rAAT flows through during the loading step. The column is equilibrated and the IMAC pool containing the product is pumped through the column after adjusting the NaCl concentration to 1.2 M using a stock solution. The product is contained in the column effluent fraction, host cell impurities bound to the resin are eluted by a wash and strip step.

4. Phenyl Boronate Pool Ultrafiltration/Diafiltration

The purpose of this step is to a) concentrate the pool and b) prepare the concentrate for loading onto the Q-Sepharose HP chromatography step by performing a buffer exchange. The Ultra/diafiltration system is operated with a 10K membrane. After buffer exchange by diafiltration the concentrated product is contained in the retentate fraction.

The term "pre-purified" as used herein includes all forms of rAAT which have been treated in a way to reduce impurities. This treatment may be for example gel electrophoresis, chromatography, gel filtration, centrifugation, filtration, precipitation, crystallization or any other method known in the art to reduce impurities.

The term "impurity" as used herein, includes any impurity originating from the production of the rAAT and may include for example host cell protein impurities, polypeptide impurities, nucleic acid impurities, buffer and salt impurities, impurities originating from the cell culture medium, product related impurities such as dimers or fragments, and combinations thereof. In a specific example of the present invention the at least one impurity of the method as defined above is a yeast cell protein (YCP) impurity. In another example of the present invention the at least one impurity of the method as defined above is selected from the group consisting of 12 kDa heat shock protein, YOL09wp, dihydroliponamide dehydrogenase, ribose 5-phosphate isomerase, rAAT fragments, cystathionine gamma-lyase, glucokinase, O-acetylhomoserine sulfhydrylase, rAAT-dimer and argininosuccinate lyase, 2-hydroxyacid dehydrogenase, hexokinase A. In still another example the at least one impurity may be a combination of yeast cell proteins which can be determined, for example, by the respective immunoglobuline combination in an ELISA (see, e.g., the ELISA described in Example 2 using a polyclonal immunoglobuline combination). The content of an impurity is usually given in weight/weight of product or weight/Unit of product. If percentage values are given, they usually refer to weight impurity per weight of product.

The anion exchange chromatography material (also designated as "resin") used in the method of the present invention does not underlie a specific restriction, as long as the above-defined impurities being removed to obtain a highly purified rAAT. According to the present invention, the resin includes any material suitable for anion exchange chromatography and is, for example, an agarose based chromatography material. In a specific example of the present invention the anion exchange material is Sepharose, which is based on modified agarose, the polysaccharide chains of which are crosslinked to form a 3-dimensional network. In a preferred example of the present invention, the anion exchange material is commercially available Q Sepharose HP. However, according to another example of the present invention, the anion exchange resin matrix is selected from the group consisting of polystyrene/divinylbenzene (e.g. available from GE Healthcare, formerly Amersham Bioscience), methacrylate type polymers (e.g. available from Tosohaas, Biorad, Merck), Cellulose (e.g. available from Millipore) and acrylic copolymers (e.g. available from PALL). Further, the resins suitable in the purification of rAAT according to the present invention are not restricted in view of their ligands and may contain any anion exchange ligand known in the art. However, according to one example of the present invention, the ligands may be selected from the group consisting of quaternary ammonium (Q), quaternary aminoethyl (QAE), dimethyl aminoethyl (DMAE) and diethylaminoethyl (DEAE), or any combination thereof. Further, according to the present invention, the resin may be any commercially available resin selected from the group consisting of Cellufine Q (Millipore), SourceQ (GE Healthcare), Fractogel EMD DEAE (Merck) and Toyopearl QAE (Tosohaas).

In one example of the present invention, the amount of the composition comprising the rAAT and the at least one impurity loaded onto the column according to step (i) of the method as defined above is in the range of about 2 to about 50 mg rAAT/ml resin, preferably in the range of 5 to 40 mg rAAT/ml resin and more preferably in the range of 10 to 30 mg rAAT/mg resin.

In one example of the present invention, the bed height of the anion exchange material in the column may be in the range of about 15 to about 35 cm, such as in the range of 18 to 30 cm. In a specific example of the present invention, the bed height of the anion exchange material may be in the range of 24±2 cm, such as 23 to 25 cm. According to the present invention, the column diameter is in the range of about 50 to about 130 cm, such as in a range of 80 to 120 cm. In a specific example, the column diameter is about 100 cm.

As used herein, the term "phosphate ions" further includes all ions derived from phosphoric acid, such as hydrogenphosphate ($HPO_4^{2-}$) and dihydrogenphosphate ($H_2PO_4^-$). For the preparation of buffers A and B of the present invention, any compound may be used suited to provide said phosphate ions, preferably phosphate salts. Those phosphate salts usable in the preparation of the phosphate buffers of the present invention should be well soluble, such as sodium or potassium phosphate. According to the nature of phosphoric acid and its dissociation constants in aqueous solution at equilibrium and neutral pH, phosphoric acid mainly exists as hydrogen- and di-hydrogenphosphate, but very low concentrations of free acid ($H_3PO_4$) or the hydrogen free base ($PO_4^{3-}$). Thus, the buffers according to the present invention may also include mixtures of different types of ions derived from phosphoric acid, such as mixtures of hydrogenphosphate and dihydrogenphosphate.

According to the present invention, the gradient used in step (iii) of the method as defined above may be a linear gradient from a buffer composition comprising 100% (v/v) of buffer A to a buffer composition of 100% (v/v) of buffer B. However, the starting composition of the gradient used in step (iii) of the above-defined method may also be any mixture of buffer A and buffer B. According to one example of the present invention, the gradient ends at a buffer composition comprising 30 to 60% (v/v) of buffer A and 70 to 40% (v/v) of buffer B. In another example of the present invention, the gradient ends at a buffer composition comprising 35 to 55% (v/v) of buffer A and 65 to 45% (v/v) of buffer B. In a specific example of the present invention, the gradient may end at a buffer composition comprising 40 to 50% (v/v) of buffer A and 60 to 50% (v/v) of buffer B.

According to the present invention, the pH of buffers A and B may be different from each other or may be the same. In one example of the present invention, the pH of buffers A and B is in the range of about 6 to about 9, preferably in the range of 7 to 8 and more preferably in the range of 7.3 to 7.8. In a specific example of the present invention the pH of buffers A and B is 7.7

The gradient used in step (iii) of the method according to the present invention may extend over a range of about 5 to about 100 column volumes (CV) of buffer solution. In one example of the present invention the gradient may extend over a range of 10 to 40 CV. According to a specific example the gradient may extend over a range of 12 to 18 CV.

According to the present invention, buffer A used in the method as defined above comprises phosphate ions in the range of about 1 to about 80 mM, preferably in the range of 20 to 50 mM and more preferably in the range of 25 to 35 mM, and N-acetylcysteine (NAC) in the range of about 0.1 to about 50 mM, preferably in the range of 1 to 30 mM and more preferably in the range of 2 to 5 mM.

Buffer B used in the method according to the present invention comprises phosphate ions in the range of about 50 to about 1000 mM, preferably in the range of 100 to 300 mM and more preferably in the range of 130 to 170 mM, and N-acetylcysteine (NAC) in the range of about 0.1 to about 50 mM, preferably in the range of 1 to 30 mM and more preferably in the range of 2 to 5 mM.

According to the present invention, buffers A and B may contain additional components such as organic and/or inorganic salts, examples of which are NaCl or Tris, as long as these additional components do not have any negative impact on the above-defined method.

The operating temperature used for the method according to the present invention does not underlie a specific limitation, and can be, for example, at about room temperature or below room temperature, such as in the range of 0 to 15° C.

The starting point for the pooling defined in step (iv) of the above-defined method may be advantageously determined by UV absorption of the eluent at a wavelength from the range of 340 to 430 nm, preferably from the range of about 380 to about 410 nm, and optionally simultaneously starting recording the beginning of the pooling at 280 nm, and the end point for the pooling may be determined by UV absorption of the eluent at 280 mn. In a specific example, the pooling in step (iv) of the method as defined above is started when the UV absorption at 395 nm of the sharp peak just preceding the rAAT main peak (see FIGS. 1 and 3) has declined to less than 10%, preferably less than 4% of the maximum absorbance. According to the present invention, the pooling in step (iv) of the method as defined above is terminated when the UV absorption at 280 nm has declined to less than 60%, preferably less than 40% of the UV absorption monitored at the beginning of the pooling.

In one specific example of the present invention, the anion exchange material in the chromatography column is a 34 µm mean Q High Performance Sepharose (Amersham Bioscience) having a packed bed height of 24±2 cm, such as in the range of 23 to 25 cm, a packing of >5000 plates/meter and wherein the column diameter is in the range of 80 to 120 cm, such as 100 cm. Optionally, a 1.2 µm Sartopure GF2 filter is used as a column pre-filter. Further, buffer A comprises 30 mM phosphate ions and 3 mM NAC at a pH of 7.7, buffer B comprises 150 mM phosphate ions and 3 mM NAC at a pH of 7.7 while the load composition comprises from 10 to 30 mg of rAAT/ml resin as well as 30 mM phosphate ions and 3 mM NAC at a pH of 7.7. After the loading step, a wash step applying buffer A was carried out to remove the unbound load material from the column and to wash off weakly bound impurities. The operating temperature ranges from 6 to 10° C. and the elution is performed using a linear gradient from 100% of buffer A to a buffer composition of 40% of buffer A and 60% of buffer B, wherein the gradient extends over a range of 15.5 to 16.5 column volumes (CV). The rAAT pooling starts when the UV absorption at 395 nm of the sharp peak just preceding the rAAT main peak has declined to less than 10% of the maximum absorbance and the UV absorption at 280 nm is recorded for the beginning of the pooling. Finally, the rAAT pooling ends when the UV absorption at 280 nm has declined to 40% of the UV absorption monitored at the beginning of the pooling.

EXAMPLES

Example 1

Purification Procedure of rAAT on QHP Resin

The bakers yeast Saccharomyces cerevisiae strain containing the plasmid for the production of rAAT is grown in a fermenter at a controlled temperature (30° C.), dissolved oxygen concentration, pH and glucose concentration for about 70 hours. After cooling the fermenter broth the cells are harvested and washed by centrifugation. The cell concentrate is resuspended in a buffer and the cells are disrupted by passing once through a high pressure homogenizer. The obtained homogenate is then clarified by microfiltration to remove particulate material followed by a buffer change. The rAAT contained in the clarified permeate is then captured by anion exchange chromatography at Q-Sepaharose XL followed by a purification step on Chelating Sepharose FF resin (Immobilized Metal Affinity Chromatography). The obtained eluate pool is then passed over a Phenyl Boronate resin operated in negative mode to further remove host cell proteins. The product contained in the column flow through fraction is then concentrated by Ultrafiltration followed by a buffer exchange by Diafiltration. This rAAT concentrate serves as the load material for the final polishing step on Q-Sepharose HP.

Column Preparation:

A column with a diameter of 11 mm (Vantage 11/500 (Millipore), equipped with a 10 µm polypropylene bed support) is packed with Q Sepharose HP according to a procedure suggested by the manufacturer. Briefly a sufficient volume of 50% gel slurry (Q Sepharose HP in 20% ethanol) is poured into the column and the resin sedimented by gravity. Following that the gel bed is packed by applying a buffer flow (20 mM Tris, pH=7.7) for about 30 minutes that causes a pressure drop at the column bed of approximately 3.5 bar. The quality of the resin packing is tested applying a HETP determination using 100 µl of a 1% aceton solution for spiking. The resulting chromatogram is analyzed and the corresponding plate numbers are calculated. The resulting column used in the purification runs according to Example 1 shows a bed height of 24.6 cm, a column volume of 23.4 ml, 2216 plates/m and an asymmetry of 2.10.

Pre-Equilibration/Equilibration:

Before loading the column is pre-equilibrated by flushing 4 column volumes (CV) of buffer B (150 mM sodium phosphate and 3 mM NAC at a pH of 7.7) over the column followed by 5 CV of buffer A (30 mM sodium phosphate and 3 mM NAC at a pH of 7.7) for equilibration.

Loading:

The load composition is a rAAT Ultra/Diaflitrate with a concentration of 13.5 mg/ml rAAT in a buffer formulation containing 30 mM phosphate and 3 mM N-acetylcysteine (NAC) at a pH of 7.7. The loading composition is then pumped through the column at a flow of 60±15 cm/h and at a temperature of 8±2° C. to reach a column load of 20.7 mg rAAT/ml anion exchange material (resin).

Washing:

Following the load cycle 3 CV of buffer A are flushed through the column at a flow of 60±15 cm/h and at a temperature of 8±2° C.

Elution:

Following the wash procedure bound rAAT is eluted from the resin applying a linear gradient with buffer A and buffer B. The start and endpoint of the gradient is from 100% (v/v) buffer A to 100% (v/v) buffer B within 27 column volumes. The column effluent is collected in fractions of approximately 5-7 ml. The pooling boundaries were defined by fraction impurity testing. At the ascending part of the peak pooling started with the fraction having a rAAT purity of larger or equal 99% of total protein, determined by HPLC and quantified by integration of the area under the peak. The UV absorption at 280 nm was 51.6 mAU, the UV adsorption at 395 nm was 2.3 mAU, which is 3.1% of the maximum adsorption detected in pre-pool E1. At the descending part of the peak pooling ended with the fraction having a rAAT dimer content as a product related impurity of less than 0.2% at a UV absorption at 280 nm of 24.3 mAU, which is 47% of the absorption at begin of pooling.

Figure 1:
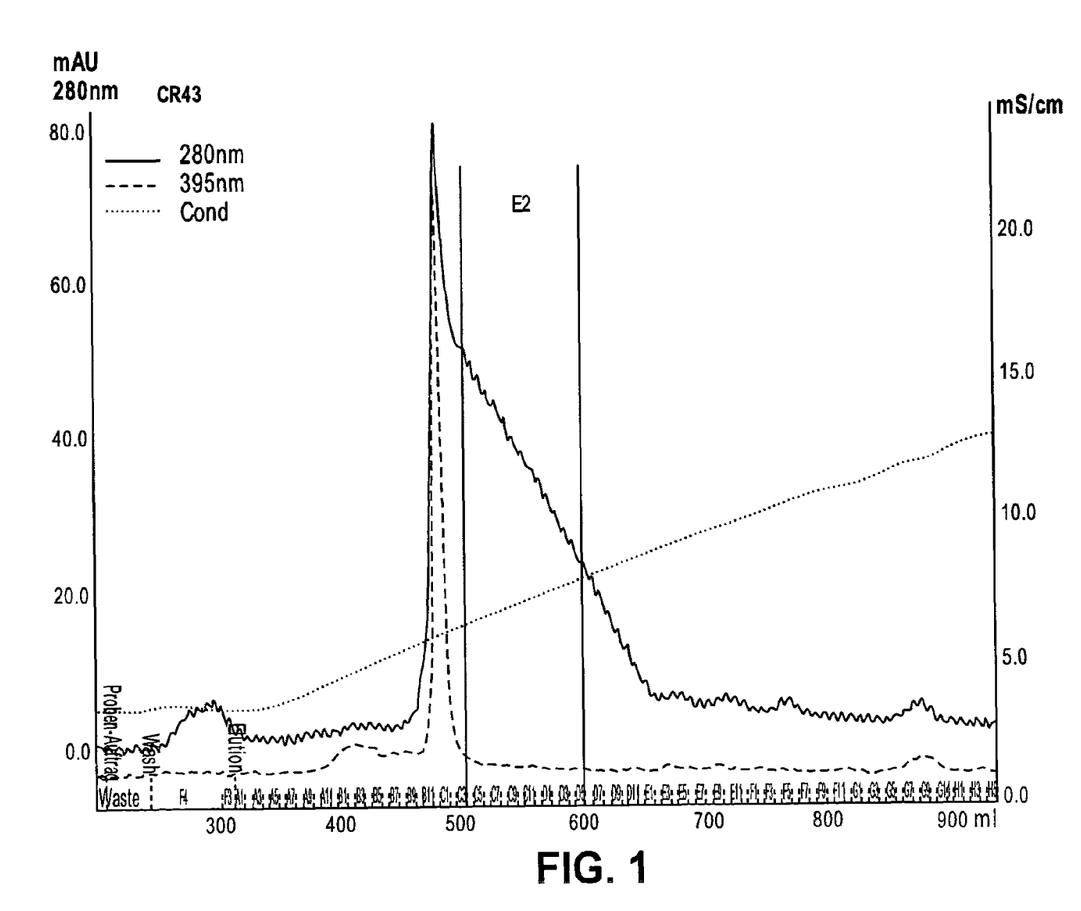
FIG. 1 shows the chromatogram of purification run according to Example 1. The chromatogram of the wash and gradient elution phase is depicted. The UV absorption signal at 280 nm is shown as solid line, the signal at 395 nm is shown as dashed line and the conductivity signal is displayed as dotted line. The borders of the main QHP pool (E2) are indicated by two vertical black lines. Due to technical reasons, the signal at 280 nm was about 7 fold lower than expected. The left vertical (y) axis shows the UV absorption in milli absorption units (mAU at 280 nm), the right vertical (y) axis shows the conductivity in mS/cm and the horizontal (x) axis shows the volume pumped (ml).

The chromatographic elution profile of the rAAT purification run according to Example 1 is shown in FIG. 1 with the borders of the main product pool (E2) indicated by vertical lines.

Example 2

The rAAT purification procedure has been carried out by the same protocol as used in Example 1, except for the following changes:
Pre-Equilibration/Equilibration:
Before loading the column is pre-equilibrated by flushing 5 column volumes (CV) of buffer B (20 mM Tris and 250 mM NaCl at a pH of 7.7) over the column followed by 4 CV of buffer A (20 mM Tris at a pH of 7.7) for equilibration.
Loading:
The load composition is a rAAT Ultra/Diaflitrate with a concentration of 27 mg/ml rAAT in a buffer formulation containing 20 mM Tris at a pH of 7.7. The loading composition is then pumped through the column at a flow of 60±15 cm/h and at a temperature of 8±2° C. to reach a column load of 11.6 mg rAAT/ml anion exchange material (resin).
Washing:
When loading is finished, the column is flushed with 3 CV of buffer A (20 mM Tris at a pH of 7.7) at a flow rate of 60±15 cm/h to displace the remaining load from the column. Then the column is washed with 4 CV of a buffer mix containing 60% (v/v) buffer A (20 mM Tris at a pH of 7.7) and 40% (v/v) buffer B (20 mM Tris, 250 mM NaCl at a pH of 7.7) at a flow rate of 60±15 cm/h to remove weakly bound impurities.
Elution:
Following the wash procedure bound rAAT is eluted from the resin applying a linear gradient with buffer A and buffer B. The gradient starts with a buffer mix containing 60% (v/v) buffer A (20 mM Tris at a pH of 7.7) and 40% (v/v) buffer B (20 mM Tris, 250 mM NaCl at a pH of 7.7) and ends with a buffer mix containing 28% (v/v) buffer A (20 mM Tris at a pH of 7.7) and 72% (v/v) buffer B (20 mM Tris, 250 mM NaCl at a pH of 7.7) performed within 27 column volumes. The column effluent is collected in fractions of approximately 5-7 ml. At the ascending part of the peak pooling started with the fraction having a rAAT purity of larger or equal than 99% of total protein, determined by HPLC and quantified by integration of the area under the peak. The UV absorption at 280 nm was 333.7 mAU, the UV adsorption at 395 nm was 0.27 mAU, which is 2.8% of the maximum adsorption detected in prepool E1. At the descending part of the peak pooling ended with the fraction having a UV absorption at 280 nm of 153.1 mAU, which is about 45% of the absorption at begin of pooling.

Figure 3:
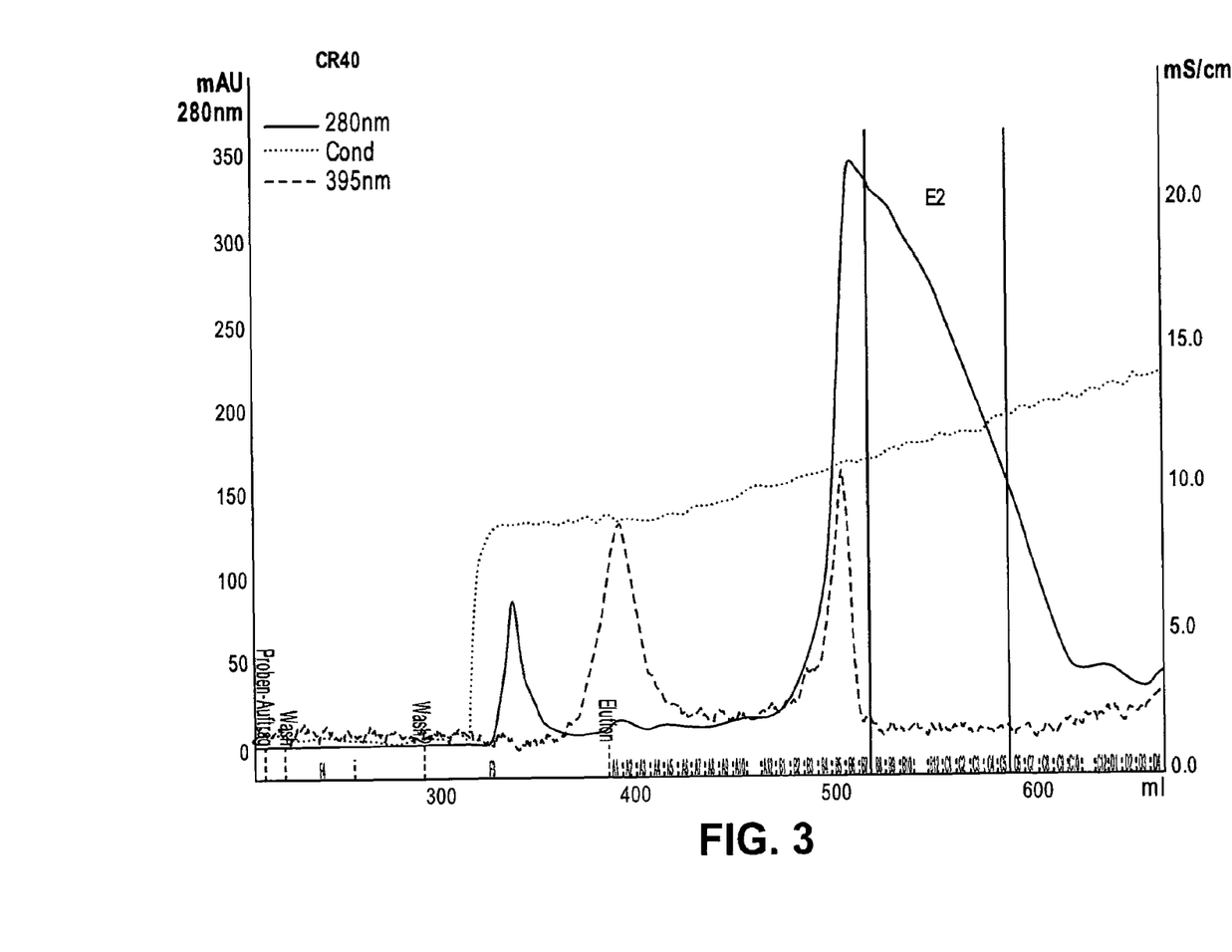
FIG. 3 shows the chromatogram of the purification run according to Example 2. The chromatogram of the wash and gradient elution phase is depicted. The UV absorption signal at 280 nm is shown as solid line, the signal at 395 nm is shown as dashed line and the conductivity signal is displayed as dotted line. The borders of the main QHP pool (E2) are indicated by two vertical black lines. The left vertical (y) axis shows the UV absorption in milli absorption units (mAU at 280 nm), the right vertical (y) axis shows the conductivity in mS/cm and the horizontal (x) axis shows the volume pumped (ml).

The chromatographic elution profile of the rAAT purification run according to Example 2 is shown in FIG. 3 with the borders of the main product pool (E2) indicated by vertical lines.

The load and buffer formulations of the purification runs according to Example 1 and Example 2 are summarized in following Table 1.

TABLE 1

| Run ID | Load | Buffer A | Buffer B | Gradient 0-100% (v/v) |
|---|---|---|---|---|
| Example 1 | 30 mM PO$_4$, 3 mM NAC, pH = 7.7 | 30 mM PO$_4$, 3 mM NAC, pH = 7.7 | 150 mM PO$_4$, 3 mM NAC, pH = 7.7 | 27 CV |

TABLE 1-continued

| Run ID | Load | Buffer A | Buffer B | Gradient 0-100% (v/v) |
|---|---|---|---|---|
| Example 2 | (UF/DF02a-G25) 20 mM Tris, pH = 7.7 (UF/DF02b) | 20 mM Tris, pH = 7.7 | 20 mM Tris, 250 mM NaCl, pH = 7.7* | 27 CV |

Table 1 shows the load and buffer formulations used in the purification runs according to Example 1 and Example 2. The pH refers to a temperature of 8±2° C. The extension-G25 in the sample code for the load indicate a buffer exchange on a G25 column. *: a retesting of the pH of the buffer resulted in 7.3.

The results of the respective purification runs according to Example 1 and Example 2 are summarized in the Table 2.

TABLE 2

| Run ID | comment | Column load (mg/ml resin) | Yield (%) | rAAT conc. (HPLC) (μg/ml) | YCP (IGEN) (μg/ml rAAT) | Hexokinase (mU/mg rAAT) |
|---|---|---|---|---|---|---|
| Example 1 | elution with a phosphate gradient, no additional salt | 20.7 | 54 | 2893 | 0.17 | 21 |
| Example 2 | Tris buffer, pH = 7.7, elution with a NaCl gradient | 11.6 | 56 | 2173 | 2.1 | 197 |

Table 2 shows comparison runs on QHP of Example 1 and Example 2. The data in the table represents the analytics of the QHP pools that were generated based on the UV signal.

Figure 2:
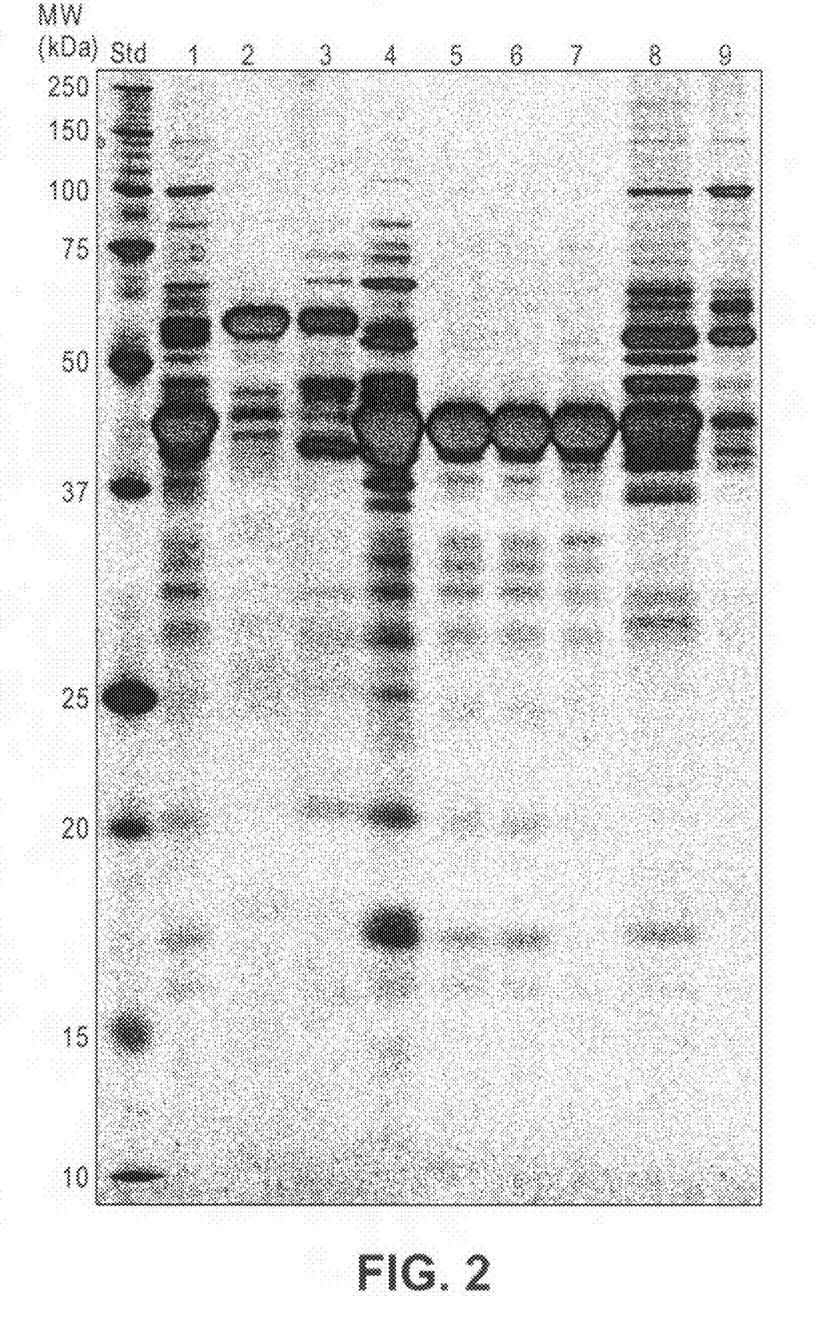
FIG. 2 shows the SDS-PAGE analysis of samples of the QHP purification run according to Example 1. Various fractions of a purification run on QHP are analysed by SDS-PAGE on a 12% gel. The separated polypeptides are visualized by silver staining. The main rAAT product is Pool E2, whereas Pool E1 represents the residual rAAT at the ascending part of the peak and Pool E3 the residual rAAT at the descending part of the peak. Approximately 4.5 µg rAAT are loaded for the E2 and E3 samples. Lane 1: load, Lane 2: flow through, Lane 3: wash, Lane 4: Pool E1, Lane 5: Pool E2, Lane 6: Pool E2 (repooled), Lane 7: Pool E3, Lane 8: Pool E4, Lane 9: Strip 1. Std.: Molecular Mass standard Precision Plus Dual Color (Biorad Laboratories).
Figure 4:
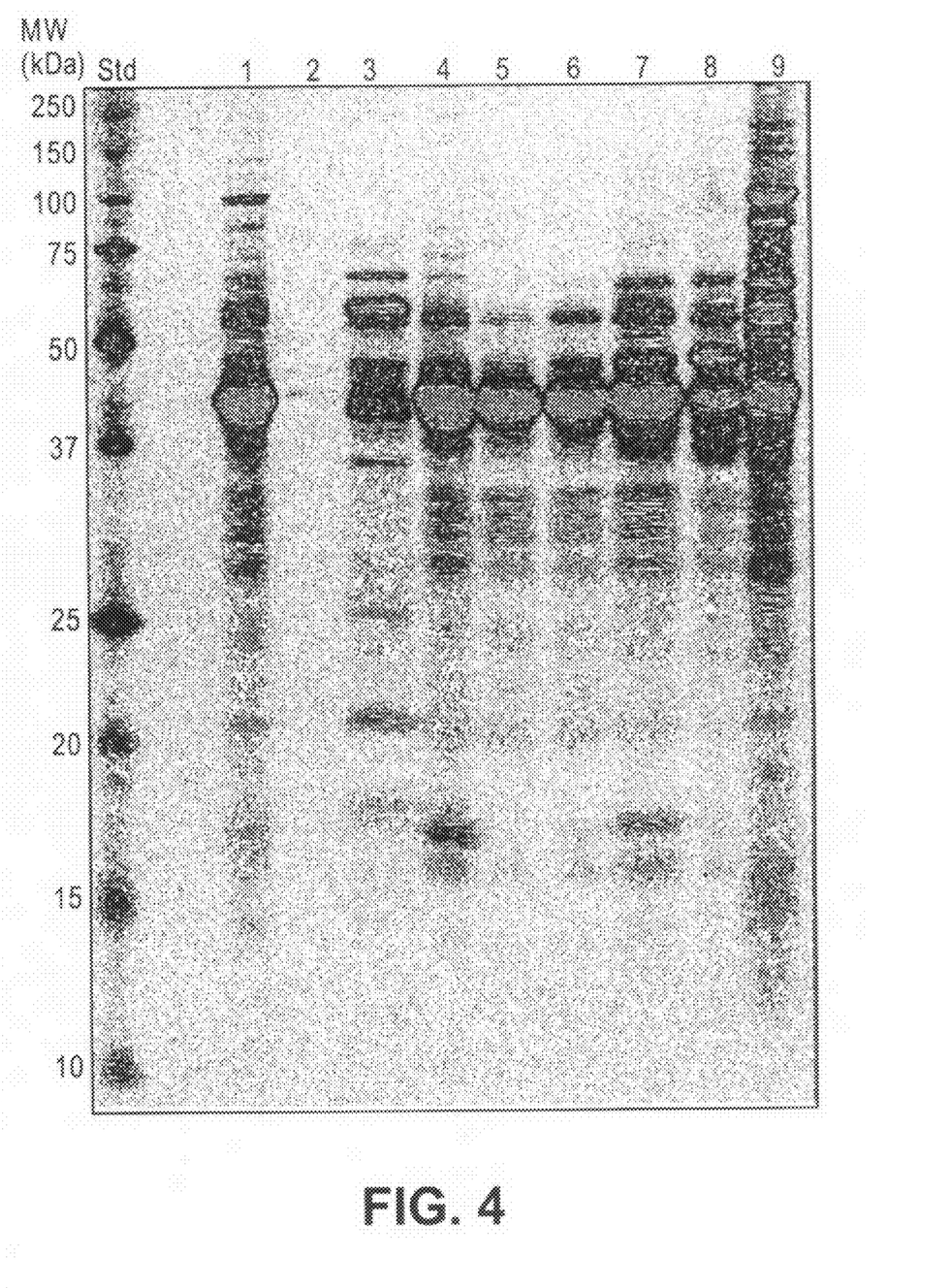
FIG. 4 shows the SDS-PAGE analysis of samples of the QHP purification run according to Example 2. Various fractions of a purification run on QHP are analysed by SDS-PAGE on a 12% gel. The separated polypeptides are visualized by silver staining. The main rAAT product is Pool E2, whereas Pool E1 represents the residual rAAT at the ascending part of the peak and Pool E3 the residual rAAT at the descending part of the peak. Approximately 4.5 µg rAAT are loaded for the E2 and E3 samples. Lane 1: load, Lane 2: flow through, Lane 3: wash, Lane 4: Pool E1, Lane 5: Pool E2, Lane 6: Pool E3, Lane 7: E4, Lane 8: Strip 1, Lane 9: Strip 2. Std.: Molecular Mass standard Precision Plus Dual Color (Biorad Laboratories)
Figure 5:
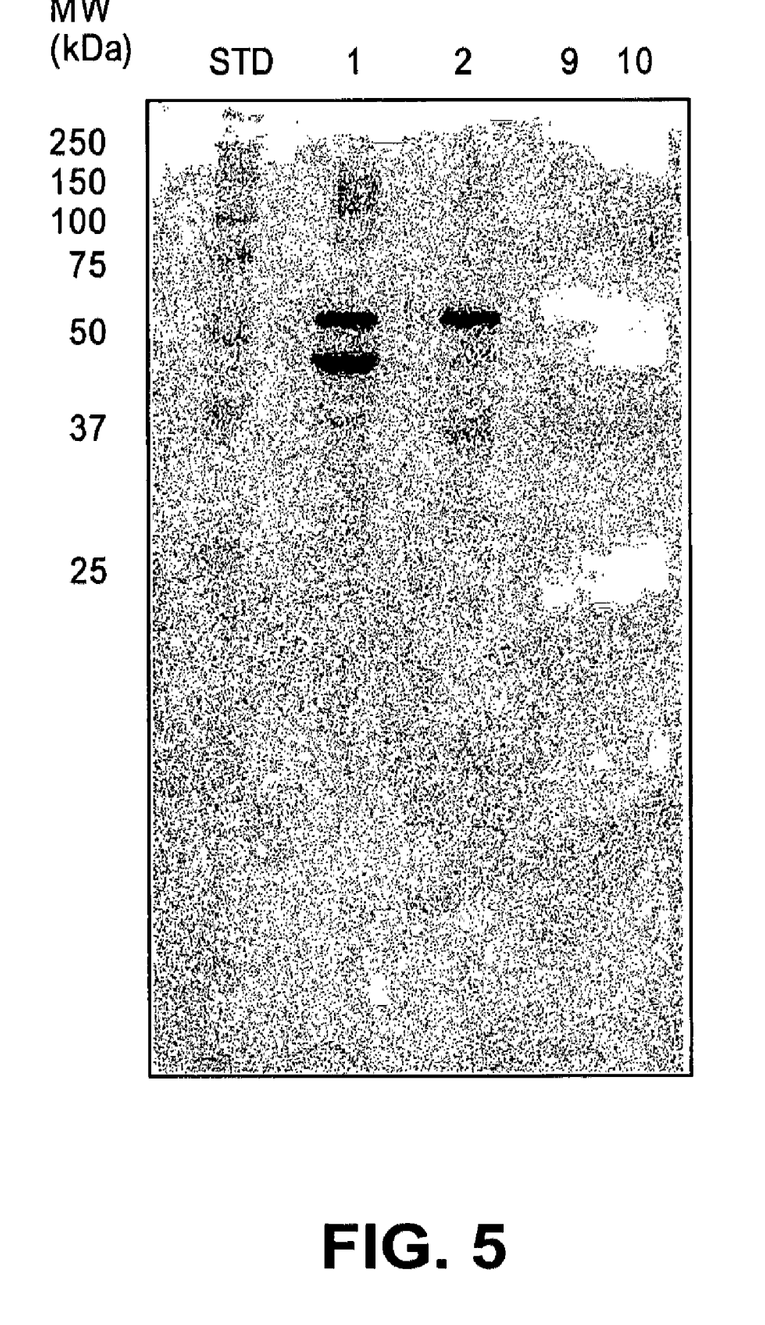
FIG. 5 shows the Anti-Yeast Cell Protein Western Blot of rAAT QHP pools (E2). rAAT QHP E2 pools (main product pools) are analysed by SDS-PAGE on a 12% gel loading approximately 12.5 µg rAAT per lane. The separated polypeptides are visualized by Western Blot Technique using goat anti-yeast cell protein Immunoglobulines for the primary detection reaction. The dark band at about 50 kDa represents Yeast Hexokinase A. Std: pre-stained molecular mass standard "Precision Plus Dual Color" (Biorad Laboratories). The fractions used for pooling are indicted in parenthesis when more than one pool was generated. Lane 1: RS-002 (control), Lane 2: Example 2-Pool E2, Lane 9: Example 1-Pool E2 (C4-D4), Lane 10: Example 1-Pool E2 (C3-D3).

For these runs the experimental set-up was kept constant including the batch of the load material, the column, the chromatography system as well as the column load that was kept in a range between 10-30 mg rAAT/ml resin. The chromatographic elution profiles of Example 1 and Example 2 are shown in FIGS. 1 and 3 with the borders of the main product pool (E2) indicated by vertical lines. The relevant analytical data of these purification runs on QHP are summarized in Table 2. However, the content of yeast host cell proteins is reduced about 12-fold in the QHP pool of Example 1 manufactured with the phosphate buffer system according to the present invention compared to the pools derived from the Tris buffer manufacture of Example 2 as determined with the IGEN Immunoligand assay (see below). Similarly, the Yeast Hexokinase activity is reduced significantly when comparing the data for rAAT pools of Example 1 (phosphate buffer) with the rAAT pool of Example 2 that was manufactured in a Tris buffer system. SDS-PAGE analyses confirm the increased purity of rAAT in the product pool (E2) of the "Phosphate" purification run (Example 1) compared to "Tris buffered" purification run (Example 2) and show in particular a significant reduction of the major impurity Yeast Hexokinase at 50 kDa. This observation can be made on both, the silver stained gels (see FIGS. 2 and 4) and the Western Blots developed for Yeast cell protein (YCP) using goat polyclonal anti-YCP Immunoglobulines (see FIG. 5). When evaluating the analytical data available for the rAAT pools of the runs according to Example 1 and Example 2, the advantageous and significant improvement in purity can be observed for the rAAT pool according to Example 1.

YCP Immunoligand Assay on IGEN (ELISA):

The yeast host cell proteins are determined by applying an immunoligand assay on a IGEN M8 Analyzer using goat polyclonal anti-yeast immunoglobulines. The detection procedure on the M8 Analyzer is performed according the instructions of the manufacturer (BioVeris Corp.). The sample is incubated with two different goat anti-yeast polyclonal immunoglobuline preparations (IgGs), where one is labelled with an electrochemoluminescence tag and the other part is labelled with biotin. After the antigen/antibody reaction the immunocomplexes are immobilized on paramagnetic beads pre-coated with streptavidin. The solution is then pumped into the detection cell and immunocomplexes are captured by magnetic forces on an electrode. The detection reaction is initiated by applying voltage causing the emission of light which is quantified and related to the content of immunodetectable yeast antigen present in the sample. For calibration of the assay a well characterized preparation of yeast host cell proteins is used.

Yeast Hexokinase Activity Assay:

Hexokinase and/or hexokinase like activity is measured using the conversion of β-nicotinamide adenosine dinucleotide phosphate (NADP) to NADPH that can be followed at 340 nm. In this reaction glucose-6-phosphat is oxidized to 6-phospho-D-gluconate by the enzyme glucose-6-phosphate dehydrogenase (G-6-PDH) with NADP as a cofactor. Glucose-6-phosphat is synthesized in an enzymatic reaction from glucose and ATP by hexokinase (or glucokinase). The procedure that is used to measure the activity of the enzyme(s) is according to a description of Sigma that refers to Bergmeyer, H. U., Grassl, M., and Walter, H. E. (1963) Methods of Enzymatic Analysis (Bergmeyer, H. U. ed. $3^{rd}$ ed., Volume II, 222-223, Verlag Chemie, Deerfield Beach, Fla.). Triethanolamine buffer, pH 7.6, glucose, adenosine 5'triphosphate (ATP), magnesium chloride, (NADP) and G-6-PDH are mixed in quarz cuvettes at 37° C. and the reaction is started by the addition of the sample. Usually four different amounts of the sample (0 μl, 2,5 μl, 5 μl, and 7,5 μl or 0 μl 10 μl, 20 μl, and 30 μl for samples with very low hexokinase content) are measured at 340 nm for 5 min. From the obtained ΔA/min the mU/ml of the samples are calculated using an molar extinctions coefficient of β-NADPH of $\epsilon=6220$ $M^{-1}$ $cm^{-1}$.

It is understood that the examples and embodiments described herein are for illustrative purposes only and that various modifications or changes in light thereof will be suggested to persons skilled in the art and are to be included within the spirit and purview of this application and scope of the appended claims. All publications, accession numbers, patents, and patent applications cited herein are hereby incorporated by reference in their entirety for all purposes.

What is claimed is:

1. A method for obtaining highly purified recombinant alpha 1-antitrypsin (rAAT) from a composition comprising the rAAT and at least one host cell protein impurity comprising hexokinase originating from cultivation of cells used for generating rAAT, the method comprising:
    (a) purifying rAAT present in the composition away from the impurity by sample displacement chromatography, comprising the steps of:
        (i) loading the composition comprising rAAT and at least one host cell protein impurity onto a column comprising an anion exchange material comprising an anion exchange ligand selected from the group consisting of quaternary ammonium and quaternary aminoethyl;
        (ii) washing the anion exchange material using a buffer comprising 1 to about 80 mM phosphate ions and 0.1 to about 50 mM N acetylcysteine (NAC);
        (iii) eluting the rAAT from the anion exchange material using a phosphate ion gradient starting with a first buffer composition comprising 1 to about 80 mM phosphate ions and 0.1 to about 50 mM NAC and ending with a second buffer composition comprising 50 to 1000 mM phosphate ions and 0.1 to 50 mM NAC, wherein the concentration of phosphate ions at the end of the gradient is greater than the concentration of phosphate ions at the beginning of the gradient, and further wherein the pH of the first and second buffer compositions is maintained between 7.3 to 7.8; thereby generating an eluent in fractions;
        (iv) collecting fractions of the eluent containing rAAT that has been purified away from the impurity; and
    (b) pooling the fractions containing purified rAAT to form an rAAT pool, wherein the rAAT pool contains at least 50% less mass of hexokinase impurity as compared to an rAAT pool generated under the same elution conditions except the elution gradient is sodium chloride in a Tris buffer.

2. The method according to claim 1, wherein the at least one impurity is a yeast host cell protein.

3. The method according to claim 1, wherein the anion exchange material is selected from the group consisting of Q Sepharose HP, Cellufine Q, SourceQ, and Toyopearl QAE.

4. The method according to claim 1, wherein step (i) comprises loading about 2 to 50 mg of rAAT per ml anion exchange material onto the column.

5. The method according to claim 1, wherein step (iii) comprises eluting the rAAT from the anion exchange material within about 30 column volumes (CV) of the gradient.

6. The method according to claim 1, wherein the starting point for the pooling in step (b) is determined by UV absorption of the eluent at a wavelength in the range of 340 nm to 430 nm and the end point for the pooling is determined by UV absorption of the eluent at 280 nm.

7. The method according to claim 6, wherein the rAAT fraction pooling starts when the UV absorption at 395 nm of the peak just preceding the rAAT main peak has declined to less than 10% of the maximum absorbance and wherein the rAAT fraction pooling is terminated when the UV absorption at 280 nm has declined to 40% of the UV absorption monitored at the beginning of the pooling.

8. The method of claim 1, wherein the phosphate ion gradients ends with a buffer composition comprising 100 to 300 mM phosphate ions.

9. The method of claim 8, wherein the phosphate ion gradients begins with a buffer composition comprising 20 to 50 mM phosphate ions.

10. The method of claim 1, wherein the rAAT is eluted from the anion exchange material within 5 to 100 column volumes of the gradient.

11. The method according to claim 1, wherein the rAAT pool contains at least 60% less mass of hexokinse.

12. The method according to claim 11, wherein the rAAT pool contains at least 70% less mass of hexokinase.

13. The method according to claim 12, wherein the rAAT pool contains at least 80% less mass of hexokinase.

* * * * *